(12) United States Patent
Mogul

(10) Patent No.: US 10,029,074 B2
(45) Date of Patent: Jul. 24, 2018

(54) STEERABLE CATHETER HANDLE WITH SLIDE LOCK

(71) Applicant: Jamil Mogul, Saratoga, CA (US)

(72) Inventor: Jamil Mogul, Saratoga, CA (US)

( * ) Notice: Subject to any disclaimer, the term of this patent is extended or adjusted under 35 U.S.C. 154(b) by 0 days.

(21) Appl. No.: 14/798,066

(22) Filed: Jul. 13, 2015

(65) Prior Publication Data

US 2017/0014600 A1  Jan. 19, 2017

(51) Int. Cl.
*A61M 25/01* (2006.01)

(52) U.S. Cl.
CPC ........ *A61M 25/0147* (2013.01); *A61M 25/01* (2013.01); *A61M 25/0105* (2013.01); *A61M 25/0133* (2013.01); *A61M 25/0136* (2013.01); *A61M 2025/015* (2013.01)

(58) Field of Classification Search
CPC .............. A61M 25/0105; A61M 25/01; A61M 25/0147; A61M 2025/015; A61M 25/0136; A61M 25/0133
See application file for complete search history.

(56) References Cited

U.S. PATENT DOCUMENTS

| 2003/0130598 A1* | 7/2003 | Manning | A61B 5/0422 600/585 |
| 2007/0282167 A1* | 12/2007 | Barenboym | A61B 1/0052 600/131 |
| 2014/0180124 A1* | 6/2014 | Whiseant | A61B 5/02055 600/467 |

* cited by examiner

*Primary Examiner* — Andrew Gilbert
*Assistant Examiner* — Courtney Fredrickson
(74) *Attorney, Agent, or Firm* — Claude A. S. Hamrick; Hamrick IP Law Office

(57) ABSTRACT

An improved handle for a steerable catheter apparatus steerably manipulated by steering wires or rods, and including an elongated housing having one end thereof adapted for attachment to the proximal end of the steerable catheter; a steering actuator carried by the housing and including an elongated lever pivotally affixed to the housing and rotatable about an axis transverse to both the length of the housing and the length of the lever and further having an end thereof attached to the steering wires or rods of the catheter to cause deformation of at least a portion of the catheter; and a locking mechanism carried by the lever for selectively locking the steering actuator in place relative to the housing during at least a portion of the time of use of the catheter apparatus.

15 Claims, 4 Drawing Sheets

STEERABLE CATHETER HANDLE WITH SLIDE LOCK

TECHNICAL FIELD

The present invention relates generally to diagnostic and treatment catheter apparatus used in the medical field, and more specifically to an improved steerable catheter handle having a locking mechanism for selectively locking the steering lever in place during use of the device.

BACKGROUND

Steerable catheter devices have been in use in the medical field for many years. As disclosed in my prior art U.S. Pat. No. 7,269,453 and as illustrated in FIGS. 1 and 2 of the following disclosure, a typical bi-directionally steerable catheters includes a handle 10 formed by a first handle part 12 and a mating second handle part 14. The two parts are joined together using suitable fastening and/or attachment means (not shown). The handle 10 is joined via a cable 16 (FIG. 2) having an end connector 18 to controlling diagnostic equipment as suggested by the dashed lines 19. A cable strain relief means 20 is included at the junction of the cable 16 and the back end of the handle 10.

A catheter body 22 is secured in a receiving joint 24 at the front of the handle 10. A catheter strain relief means 26 is included at the receiving joint 24 to reduce the chances of breakage of the catheter body 22. Signal wires 28 (FIG. 2) from ring electrodes leading to ring shaped cathodes (not shown) pass through the interior of the catheter body 22, the handle 10, and the cable 16.

The steering capability of the catheter device is provided in this version by a steering lever 30. The steering lever 30 is mounted on a pivot 32 within the handle 10. The ends of the steering lever 30 protrude from the handle 10 through slots 34. In the illustrated device, the slots 34 are sealed with rubber strips 35 having a longitudinally extending slit 33 formed therein through which the handle 30 passes. The rubber seals also serve as a frictional position securing means for the steering lever 30.

As shown in FIG. 2, the steering mechanism of the bi-directionally steerable catheter includes as a key component a continuous length of steering wire 36 that extends out of the proximal end of the catheter body 22 and has its respective ends 38 secured to the steering lever 30. In the illustrated device, the ends 38 of the steering wire 36 are affixed to the steering lever 30 on opposite sides of the pivot 32 by suitable securing means 40 such as set screws or the like. The distal end (not shown) of the bi-directionally steerable catheter body 22 may therefore be deformed, i.e., steered, in opposite directions by rotational manipulation of the steering lever 30 about the pivot 32. Full coverage of the vessel or organ being examined by the device is thus obtained as the operator rotates both the lever and the handle 10 which in turn deflects or steers the distal end portion of the catheter body 22.

As mentioned above, in this embodiment, frictional engagement between the handle side surfaces and the rubber strips 35 is relied upon to hold the lever in position relative to the handle should the operator release his thumb or other finger pressure on the an end of the lever 30. This solution to lever position retention has however been found problematic and leading to fatigue and potential cramping in cases where the operator works with the device for an extended period of time.

In FIG. 3 of the Drawing, another embodiment of a prior art catheter handle having a similar lever design is shown in my Prior art U.S. Pat. No. 7,122,020, the disclosure of this patent as well as the above mentioned patent being incorporated herein by reference. In this prior art embodiment, the handle and steering lever designs have been modified to be more ergonomically friendly to the user. However, this handle design still relies upon lever side engagement with a pesilient friction surface to maintain lever position relative to the handle.

It is therefore an object of the present invention to provide an improved handle/lever positioning design that is more reliable than that of the previous designs.

Another object of the present invention is to provide an improved handle/lever positioning design that does not require that the user resist the friction force used to maintain positional control of the lever.

Still another object of the present invention is to provide an improved handle/lever positioning design that enables the user of the device to selectively lock the lever in a desired position.

Yet another object of the present invention is to provide an improved handle/lever positioning design that enables the user of the device to selectively lock and unlock the lever in a desired position by applying a simple transverse force to a slide locking mechanism.

SUMMARY OF THE INVENTION

These and other objectives of the present invention are achieved by modifying at least one end of the rotatable steering lever to include a simple transversely movable slide bar having a ramped lower surface configured such that when the bar is moved in one direction it clears the top surface of the device housing, but when the bar is moved in the opposite direction, it frictionally engages a top surface of the device handle thereby locking the steering lever in place. In addition, ergonomically shaped end caps are affixed to each end of the slide bar to facilitate its finger or thumb engagement by the user to move it between the unlocked and locking positions.

An important advantage of the present invention is that it makes actuation of the steering lever easier since no substantial locking friction force in the longitudinal direction must be overcome in steering the catheter.

Another advantage of the present invention is that the only use of friction force to lock the steering lever in place is when the user desires to perform a locking function.

Still another advantage of the present invention is that a more positive lock of the steering lever is afforded by the engagement of the locking bar with the upper surface of the handle housing.

These and other objects and advantages of the present invention will become apparent to those skilled in the art after a reading of the following disclosure which makes reference to the several Figures of the Drawing.

DETAILED DESCRIPTION OF EMBODIMENTS OF THE PRESENT INVENTION

Figure 1:
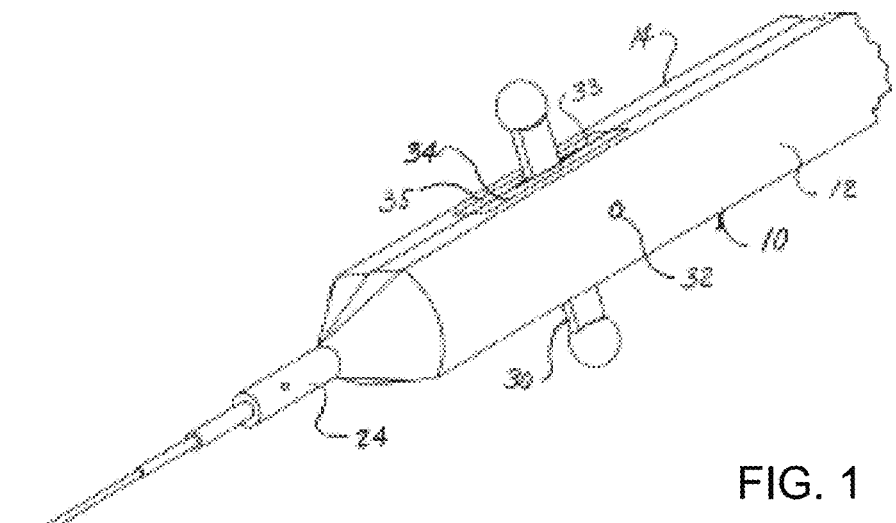
FIGS. 1-3 are depictions of two Prior art catheter steering devices.
Figure 2:
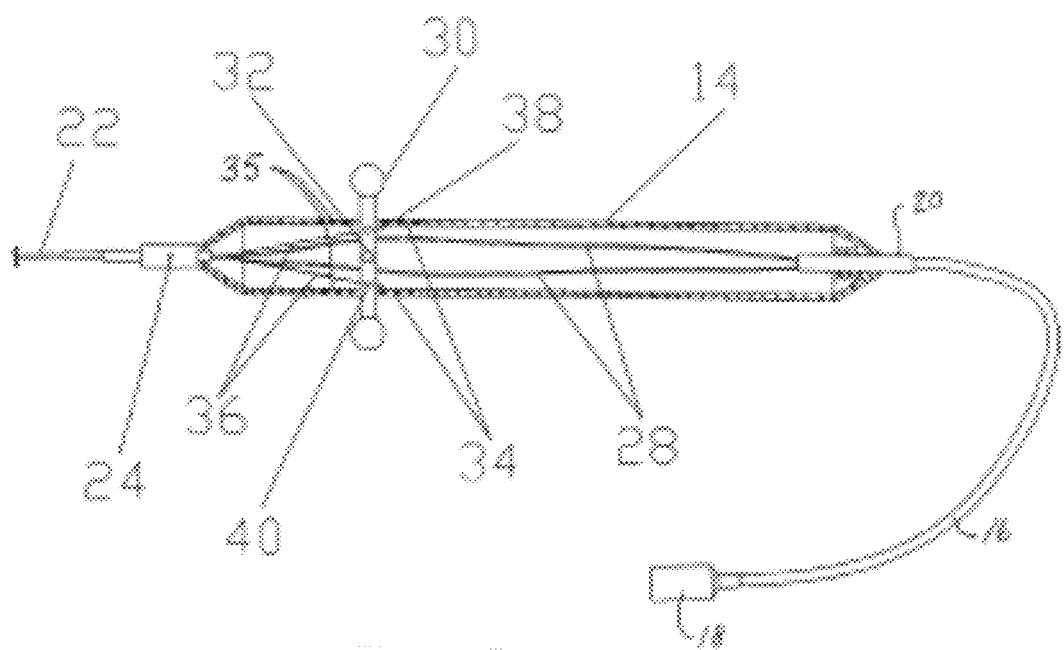
Figure 3:
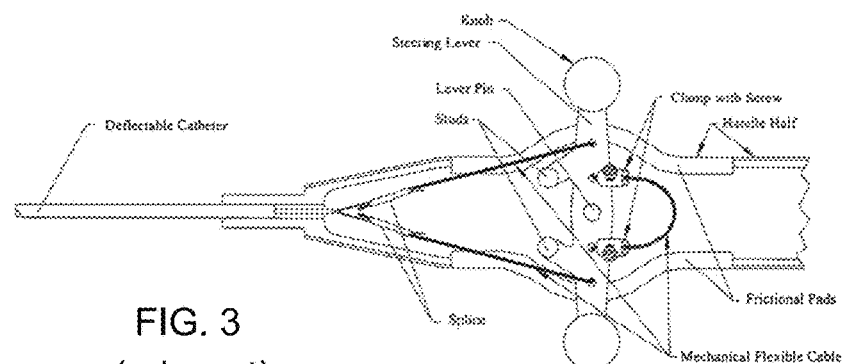
Figures 4, 5:
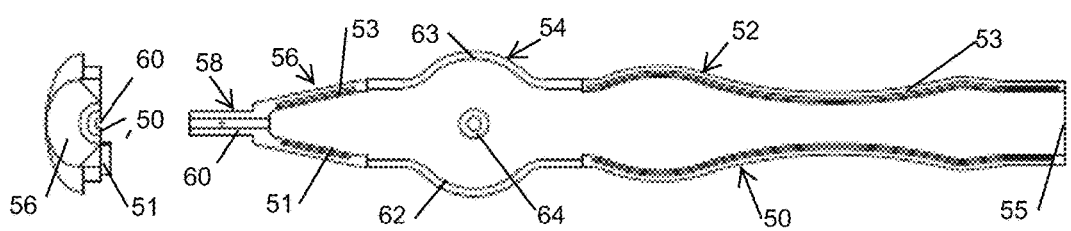
FIGS. 4-6 are respectively side elevation, top view and distal end views of an embodiment of the present invention.
Figure 6:
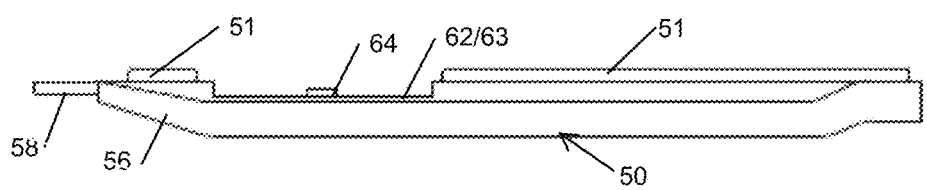

Referring now to FIGS. 4-6 of the Drawing, FIG. 4 depicts at 50 a side elevational view of one of two substantially mirror imaged and mating housing parts adapted to form a handle for a steerable catheter apparatus, and shows details of the inside surfaces of the injection molded housing part. Each housing part includes a user gripping portion 52, a steering actuator or lever receiving and mounting portion 54 and a distal end portion 56 including a sub-portion 58 forming one half of a cylindrical passageway 60 for receiving the proximal end of an elongated catheter tube and its electrical and steering wire accoutrements (not shown). Note that the opposite end 55 of the part is open so that when the two parts are mated together an open passageway is formed for signal wires (not shown).

Along the side edges of the portions 50 and 56 are ribs 51 and matching slots 53 which align the two identical parts 50 that when mated together form the outer housing of the handle device.

At the center of the portion 54 is a circular standoff 64 that in each part forms a receptacle for receiving an end of an axel pin (not shown) about which the steering lever will rotate. The outer edges 62 and 63 (FIG. 4) of the portion 54 of the elongated steering lever 70 are formed concentric with the axis of the pin, i.e., the center of rotation of the lever 70 and are undercut as indicated at 62/63 in FIG. 6 so as to form elongated top and bottom slots through which the lever extends when the device is assembled.

Figures 7, 8, 9:
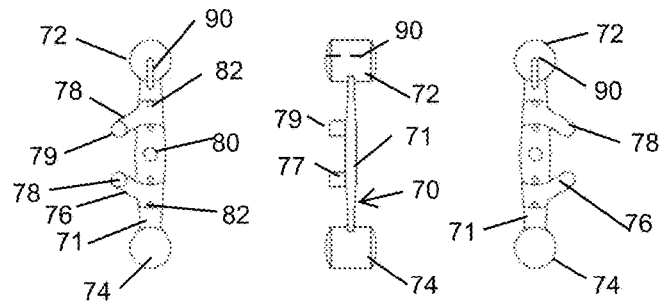
FIGS. 7-9 are respectively front, left side and right side elevations of a steering lever component of an embodiment of the present invention.
Figure 11:
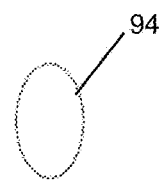
FIGS. 10-12 are respectively transverse left side and right side elevations of a locking slide component of an embodiment of the present invention.

FIGS. 7-9 show details of a steering lever 70 which includes an elongated lever arm 71 with the upper and lower ends thereof respectively terminating in a barrel shaped knob or the like 72 and 74. Extending from the arm 71 in the distal direction are tabs 76 and 78 supporting laterally extending studs 77 and 79 which engage the steering wires or rods (not shown) of the catheter to increase the mechanical advantage of the lever. Note that lever arm has several apertures provided therein; namely, a central pivot opening 80 for receiving the pivot pin mentioned above, and a plurality of steering wire or rod attachment openings 82 for facilitating attachment of the top and bottom steering wires or rods (not shown). In addition, at the top end of the arm 71 and extending into the upper knob 72 is a slot 90 that extends along the full length of the knob to provide a passageway for receiving a locking slide.

Figure 10:
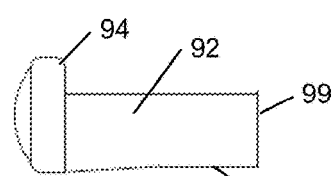
Figure 12:
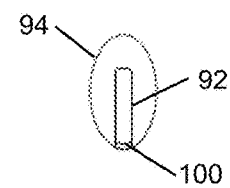
Figure 14:
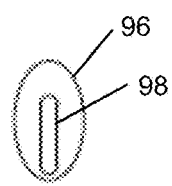
FIGS. 13-15 are respectively transverse left side and right side elevations of a locking slide end cap component of an embodiment of the present invention.
Figure 13:
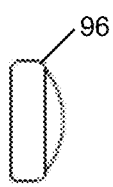
Figure 15:
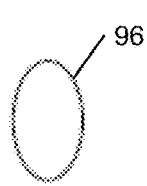

Turning now to FIGS. 10-15 details of the locking slide are depicted and include an elongated and tapered slide bar or member 92 of rectangular cross section, and a pair of end oval shaped caps 94 and 96. Alternatively, the slide bar or member 92 could be of oval or other geometrical cross sectional shape adapted to mate with a corresponding passageway configuration adapted to provide a locking function corresponding to that described herein. Note that the back side of cap 96 is provided with a slot 98 for receiving the end 99 of the slide 92 after it is inserted into the slot 90 (FIGS. 7-9). Note also that the bottom edge 100 of slide 92 is tapered from left to right as best depicted in FIG. 10.

Figure 18:
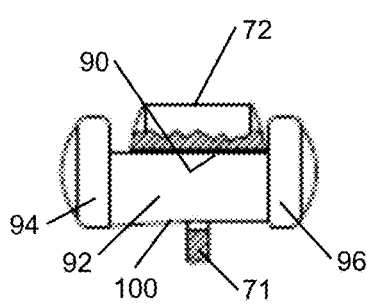
FIG. 18 is a transverse cross section taken along the line 18-18 of FIG. 17.
Figure 17:
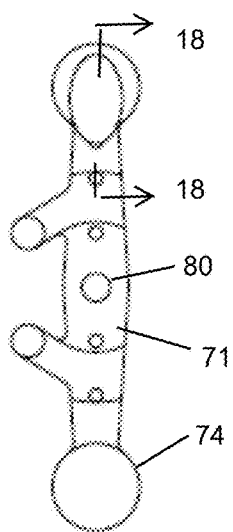
FIGS. 16 and 17 are respectively transverse and left side elevations of a steering lever and locking slide component assembly of an embodiment of the present invention.
Figure 16:
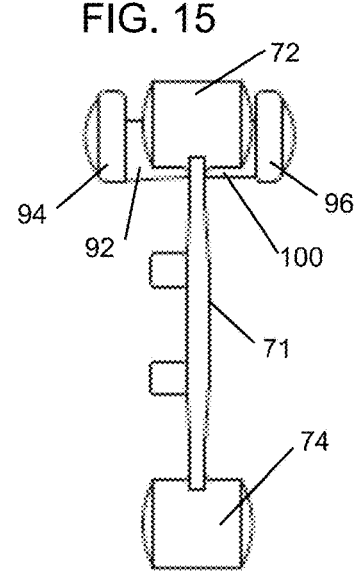

FIGS. 16 and 17, and the partially broken cross section of FIG. 18 show the locking slide 92 inserted into the slot 90, and the end cap 96 affixed thereto by either a press-fit or the use of a suitable glue or the like. The views of the lever 71 and locking slide 92 shown in FIGS. 16 and 18 are taken looking toward the distal end of the device to show the slide lock configured for a right handed user, i.e., configured so that the user can use his thumb to apply a locking force to the slide lock.

Figures 19, 20:
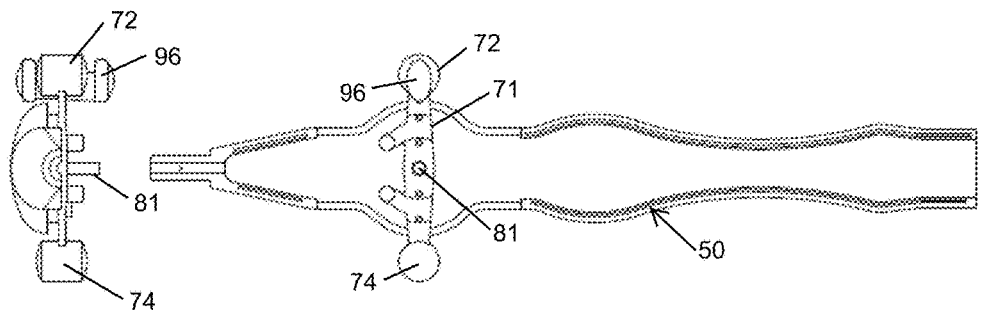
FIGS. 19 and 20 are respectively left side and transverse end elevations of a steering lever and housing side component assembly of an embodiment of the present invention.
Figures 21, 22:
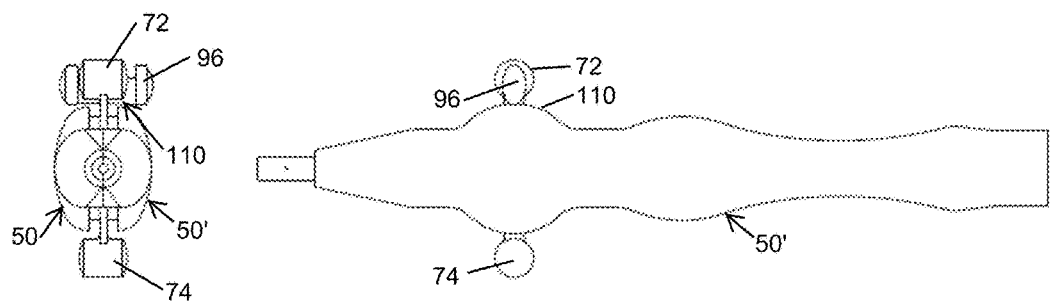
FIGS. 21 and 22 are respectively left side and transverse end elevations of a steering actuator or lever, locking slide and housing side component assembly of an embodiment of the present invention.

The progression of the final assembly (sans catheter, steering wires and electrical signal wires) is depicted in FIGS. 19-21.

Figures 23, 24:
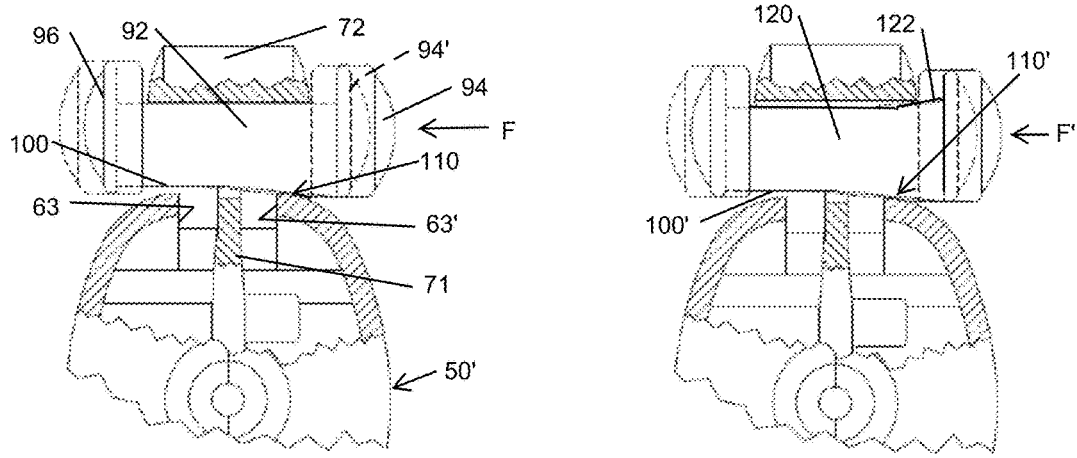
FIG. 23 is a stylized and partially broken transverse end elevational view of the assembled component embodiment illustrated in FIGS. 1-22.
FIG. 24 is a stylized and partially broken transverse end elevational view of an assembled component embodiment including a modified slide component in accordance with an embodiment of the present invention.

In FIG. 23, the lever locking function is depicted in a partially broken view taken from the distal end of the handle assembly looking back toward the lever mechanism.

With the locking slide 92 positioned to the right most extreme of its motive position (as shown by the solid lines in FIGS. 23 and 24), it will be appreciated that the narrow vertical dimension on the leftmost end of the tapered slide is positioned above the left side of the elongated lever slot defined by the opposing housing edges 63-63' (see also FIGS. 4 and 19) with the result that the tapered edge 100 makes little or no substantial frictional or "braking" contact with either side of the upper housing surface 110 circumscribing lever slot 63-63' (see FIGS. 23 and 24), and thereby permits the steering lever 71 to be freely rotated about its pivot pin 81 (see FIGS. 19 and 20) toward and away from the viewer of FIGS. 23 and 24. But once the user decides to lock the lever 71 in position relative to the handle 50-50' he merely engages his thumb with the end cap 94 affixed to the rightmost end of the slide 92 and applies enough pressure (as suggested by the force arrow F) to the slide assembly to move it leftwardly, as depicted by the dashed lines 94' in FIGS. 23 and 24, until the thicker portion of the slide member surface 100 frictionally engages with braking functionality) the upper surface (at 1101 of the housing 50' and firmly locks the lever 71 in position relative thereto. To unlock the lever 71, the user merely applies an oppositely directed force to the end cap 96 to drive the slide member back toward the right and out of substantial frictional engagement with the handle surface identified by the arrow 110.

In FIG. 24, an alternative embodiment of the slide member is depicted to show that in addition to, or perhaps even in place of, the lower surface taper of the slide member surface 100', the upper surface of the slide member, or at least a short portion 122 of the length thereof, may be tapered to engage the overlying surface of the carrying knob 72 and drive the slide member 120 downwardly as it is moved leftwardly into a locking position engaging the housing proximate the slot edge at 110'.

In the illustrated device, the lever relieving slots at the top and bottom of the handle housing are shown as being open slots. However, it is to be understood that these slots could be closed by a slitted resilient member similar to that used in the prior art mentioned above to provide a dust shield, or perhaps apply a minimal motion resistance force to the sides of the lever.

Although the present invention has been described above in terms of actual embodiments believed to be representative thereof, it is intended that the disclosure not be considered limiting and that the true scope of the invention be as broad as can be determined by a fair interpretation of the following claims.

The invention claimed is:

1. A handle for a catheter apparatus steerably manipulatable by steering wires or rods extending from the proximal end of a steerable catheter lumen, comprising:
    an elongated housing having one end thereof adapted for attachment to the proximal end of a steerable catheter lumen, said housing having an elongated slot formed in one side thereof and extending along a portion of a length of the housing;
    a steering actuator carried by said housing and adapted for attachment to the steering wires or rods of the catheter lumen, said steering actuator having a user engageable part thereof extending out of said elongated slot, said user engageable part being movable along a length of said elongated slot to facilitate differential displacement of the steering wires or rods to cause steering deformation of at least a portion of the catheter lumen; and
    a locking mechanism for selectively locking the steering actuator in place relative to the housing during use of the catheter apparatus, said locking mechanism being disposed outside of said housing and carried by said user engageable part in close proximity to a portion of an outer surface of said housing surrounding said elongated slot, said locking mechanism including an elongated locking slide member carried by said user engageable part and disposed to extend in a transverse direction relative to the length of said elongated slot, said locking slide member being lengthwise moveable in said transverse direction between a steering actuator locking position and a steering actuator unlocking position, said locking slide member being tapered along at least a portion of its length, said tapered portion being operative to cause said slide member to frictionally engage said outer surface of said housing surrounding said elongated slot when said slide member is moved to said locking position, and to disengage said outer surface of said housing when said slide member is moved to said unlocking position.

2. A handle for a steerable catheter apparatus as recited in claim 1, wherein said steering actuator includes an elongated lever extending through said slot, said lever being pivotally affixed to said housing and rotatable about an axis extending transverse to the lengths of said lever and said housing.

3. A handle for a steerable catheter apparatus as recited in claim 2 wherein the outer surface of said housing immediately circumscribing said slot is formed to lie on a generally cylindrical locus concentric with the axis about which said lever rotates.

4. A handle for a steerable catheter apparatus as recited in claim 3 wherein said locking slide member includes a bar that is tapered from one end to the other, and wherein said user engageable part includes a generally barrel shaped knob having a slot provided therein forming a passageway along which the tapered bar may be moved to alternately engage and disengage said outer surface of said housing.

5. A handle for a steerable catheter apparatus as recited in claim 1, wherein said steering actuator includes an elongated lever pivotally affixed at its midpoint to said housing and rotatable about an axis transverse to the lengths of said lever and said housing, said lever further including another user engageable part extending out of another slot formed in an opposite side of said housing.

6. A handle for a steerable catheter apparatus as recited in claim 5 wherein said user engageable parts of said steering actuator include knobs affixed to each end of said elongated lever, and wherein at least one of said knobs include a slot formed therein having said locking slide member moveably disposed therein.

7. A handle for a steerable catheter apparatus as recited in claim 6 wherein each end of said locking slide member includes a user engageable end cap affixed thereto.

8. A handle for a steerable catheter apparatus as recited in claim 1, wherein each end of said locking slide member includes an end cap for engagement by the thumb or finger of a user to facilitate locking or unlocking of said locking mechanism.

9. A catheter apparatus comprising:
    a steerable catheter lumen including a plurality of steering wires or rods extending along a length thereof;
    an elongated handle including a housing having one end thereof adapted for attachment to the proximal end of said steerable catheter lumen;
    a steering actuator carried by said housing and adapted for attachment to the steering wires or rods of the catheter lumen, said steering actuator having at least one user engageable part thereof extending out of an opening formed in said housing and movable in a longitudinal direction relative to the length from the proximal end of said housing to the distal end of said housing to facilitate differential displacement of the steering wires or rods to cause steering deformation of at least a portion of the catheter lumen; and
    a locking mechanism for selectively locking the steering actuator in place relative to the housing during use of the catheter apparatus, said locking mechanism being disposed outside of said housing and carried by said user engageable part in close proximity to a portion of an outer surface of said housing surrounding said opening, said locking mechanism including an elongated locking slide member carried by said actuator and moveable by the user in one direction to frictionally engage said outer surface of said housing to lock said steering actuator relative to said housing, and movable by the user in another direction to disengage said locking slide member from said outer surface of said housing to unlock said steering actuator, said elongated slide member being tapered from one end thereof to the other, and moveable in its longitudinal direction generally normal to the direction of movement of said steering actuator, said slide member being adapted to make no more than minimal contact with said outer surface of said housing at one extreme of its longitudinal movement, and to make substantial frictional engagement with said surface at an opposite extreme of its movement thereby locking said actuator in place relative to said housing.

10. A catheter apparatus as recited in claim 9, wherein said steering actuator includes an elongated lever extending through said opening, pivotally affixed to said housing, and rotatable about an axis transverse to the lengths of said lever and said housing.

11. A catheter apparatus as recited in claim 10, wherein the outer surface of said housing immediately circumscribing said opening is formed to lie on a generally cylindrical locus concentric with the axis about which said lever rotates.

12. A catheter apparatus as recited in claim 11, wherein said locking slide member includes a bar that is tapered from one end to the other, and wherein said user engageable part includes a barrel shaped knob having a slot provided therein, said slot forming a passageway along which the tapered bar may be moved to alternately engage and disengage said outer surface of said housing.

13. A catheter apparatus as recited in claim 9, wherein said steering actuator includes an elongated lever pivotally affixed at its midpoint to said housing and rotatable about an axis transverse to the length of said lever, said lever further including another user engageable part extending out of another opening formed in the opposite side of said housing.

14. A catheter apparatus as recited in claim 13 wherein said user engageable parts of said steering actuator include a knob affixed to each end of said elongated lever, and wherein at least one of said knobs includes a slot formed therein, said slot having said locking slide member moveably disposed therein.

15. A catheter apparatus, comprising:
  a steerable catheter lumen including a plurality of steering wires or rods extending along a length of said lumen;
  an elongated handle including a multi-part housing having one end thereof adapted for attachment to the proximal end of said lumen;
  a steering actuator carried by said housing and adapted for attachment to the steering wires or rods of said lumen, said steering actuator having at least one user engageable part thereof extending out of an opening formed in one side of said housing, said part being movable in a longitudinal direction relative to the length from the proximal end of said housing to the distal end of said housing to facilitate differential displacement of the steering wires or rods to cause steering deformation of at least a portion of the lumen; and
  a locking mechanism for selectively locking the steering actuator in place relative to the housing during at least a portion of the time of use of the catheter apparatus, said locking mechanism being disposed outside of said housing and carried by said user engageable part in close proximity to a portion of an outer surface of said housing surrounding said opening, said locking mechanism including an elongated locking slide member carried by said user engageable part, said locking slide member being tapered along at least a portion of its length and moveable in one longitudinal direction generally normal to the direction of movement of said steering actuator to frictionally engage said outer surface of said housing to lock said actuator, and being movable by the user in another longitudinal direction opposite to said one longitudinal direction to make no more than minimal contact at another extreme of its longitudinal movement and thereby disengage said locking slide member from said outer surface to thereby unlock said steering actuator.

* * * * *